United States Patent
Sugimura et al.

(10) Patent No.: US 7,135,028 B2
(45) Date of Patent: Nov. 14, 2006

(54) BLADE FOR CORNEAL SURGERY AND CORNEAL SURGICAL APPARATUS COMPRISING THE SAME

(75) Inventors: Masahiro Sugimura, Aichi (JP); Masanori Amano, Aichi (JP)

(73) Assignee: Nidek Co., Ltd., Aichi (JP)

( * ) Notice: Subject to any disclaimer, the term of this patent is extended or adjusted under 35 U.S.C. 154(b) by 686 days.

(21) Appl. No.: 10/316,044

(22) Filed: Dec. 11, 2002

(65) Prior Publication Data
US 2003/0130676 A1 Jul. 10, 2003

(30) Foreign Application Priority Data
Dec. 12, 2001 (JP) ............ P2001-378692
Dec. 12, 2001 (JP) ............ P2001-379251

(51) Int. Cl.
*A61B 17/32* (2006.01)
(52) U.S. Cl. ................................ 606/166
(58) Field of Classification Search ........ 606/166, 606/167, 185, 161, 107, 172
See application file for complete search history.

(56) References Cited

U.S. PATENT DOCUMENTS

| 4,662,370 A | 5/1987 | Hoffmann et al. |
| 5,352,233 A | 10/1994 | Anis |
| RE35,421 E | 1/1997 | Ruiz et al. |
| 5,595,570 A | 1/1997 | Smith |
| 5,624,456 A | 4/1997 | Hellenkamp |
| 5,700,274 A * | 12/1997 | Feaster ............. 606/166 |
| 5,964,776 A | 10/1999 | Peyman |
| 5,980,543 A | 11/1999 | Carriazo et al. |
| 6,056,764 A * | 5/2000 | Smith ............. 606/167 |
| 6,149,661 A | 11/2000 | Graczyk |
| 6,203,555 B1 | 3/2001 | Amano et al. |
| 6,527,788 B1 * | 3/2003 | Hellenkamp ............. 606/166 |

FOREIGN PATENT DOCUMENTS

| EP | 0 956 840 A2 | 11/1999 |
| EP | 1 092 515 A1 | 4/2001 |
| EP | 1 114 628 A2 | 7/2001 |
| WO | WO 01/45607 A1 | 6/2001 |

\* cited by examiner

*Primary Examiner*—Kevin T. Truong
(74) *Attorney, Agent, or Firm*—Finnegan, Henderson, Farabow, Garrett & Dunner, L.L.P.

(57) ABSTRACT

A blade for corneal surgery for separating a corneal epithelium in a flap shape, includes: upper and lower blade surfaces; and an edge surface connecting the upper and lower blade surfaces, the edge surface having a height of 1 to 70 μm and a connecting portion with each of the upper and lower blade surfaces having a curved surface.

8 Claims, 13 Drawing Sheets

W9

BLADE FOR CORNEAL SURGERY AND CORNEAL SURGICAL APPARATUS COMPRISING THE SAME

BACKGROUND OF THE INVENTION

1. Field of the Invention

The present invention relates to a blade for corneal surgery which is suitable for separating (incising) a corneal epithelium like a flap and a corneal surgical apparatus comprising the blade.

2. Description of the Related Art

There has been known LASIK (Laser in Situ Keratomileusis) for the keratorefractive surgery in which a flap is formed by incising a corneal portion with a thickness of about 0.15 mm ranging from a corneal epithelium to a corneal stroma with a part of the cornea remaining connected like a hinge, ablating the corneal stroma in a refractive correction amount by a laser beam, and returning the flap. In the LASIK, there is used a corneal surgical apparatus called a microkeratome which serves to incise the cornea in a layered form.

In recent years, attention has been paid to a method of LASEK (Laser Epithelial Keratomileusis) in which a corneal epithelium except a hinge is cut in an annular by an epi-trephine, and the corneal epithelium is immersed in alcohol and is swollen, and a flap is formed by separating the corneal epithelium from a Bowan's membrane by means of a golf knife, and a corneal stroma is ablated by a laser beam and the flap into an original position is returned. The LASEK cart also be applied to a thin cornea to which the LASIK cannot be applied.

Furthermore, there has been proposed a method of separating a corneal epithelium by means of a thin wire (a line diameter of approximately 50 μm) to form a flap without using alcohol.

However, the use of the alcohol may damage a cornea and a great deal of time and labor is required for forming a flap by means of a golf knife. Moreover, the tensile strength of the wire is required for forming a flap by means of a wire. If the wire is thickened to increase the strength, it is hard to smoothly separate the corneal epithelium.

SUMMARY OF THE INVENTION

In consideration of the problems of the conventional art, the invention has a technical object to provide a blade for corneal surgery which can form a corneal epithelium flap easily and smoothly without using alcohol, and a corneal surgical apparatus comprising the blade.

In order to attain the object, the invention is characterized by the following structure.

(1) A blade for corneal surgery for separating a corneal epithelium in a flap shape, comprising:
   upper and lower blade surfaces; and
   an edge surface connecting the upper and lower blade surfaces, the edge surface having a height of 1 to 70 μm and a connecting portion with each of the upper and lower blade surfaces having a curved surface.

(2) The blade according to (1), wherein the curved surface in the connecting portion has a radius of curvature of 0.5 to 35 μm.

(3) The blade according to (1), wherein an angle formed by the upper and lower blade surfaces is 10 to 70 degrees.

(4) The blade according to (1), wherein
   the height of the edge surface is 1 to 50 μm,
   an angle formed by the upper and lower blade surfaces is 10 to 50 degrees, and
   a radius of curvature of the curved surface in the connecting portion is 0.5 to 25 μm.

(5) A corneal surgical apparatus having the blade according to (1) further comprising a holder for detachably holding the blade.

(6) The corneal surgical apparatus according to (5), further comprising:
   an oscillating unit which laterally oscillates the blade, and
   a translating unit which moves and translates the blade in a direction of separation.

(7) The corneal surgical apparatus according to (6), wherein a lateral oscillation frequency is 5,000 to 25,000 rpm and a translating speed is 0.4 to 6 mm/sec.

In the present disclosure relates to the subject matter contained in Japanese patent application Nos. 2001-375692 (filed on Dec. 12, 2001) and 2001-379251 (filed on Dec. 12, 2001), which are expressly incorporated herein by reference in their entireties.

DESCRIPTION OF THE PREFERRED EMBODIMENT

First Embodiment

Figure 1:
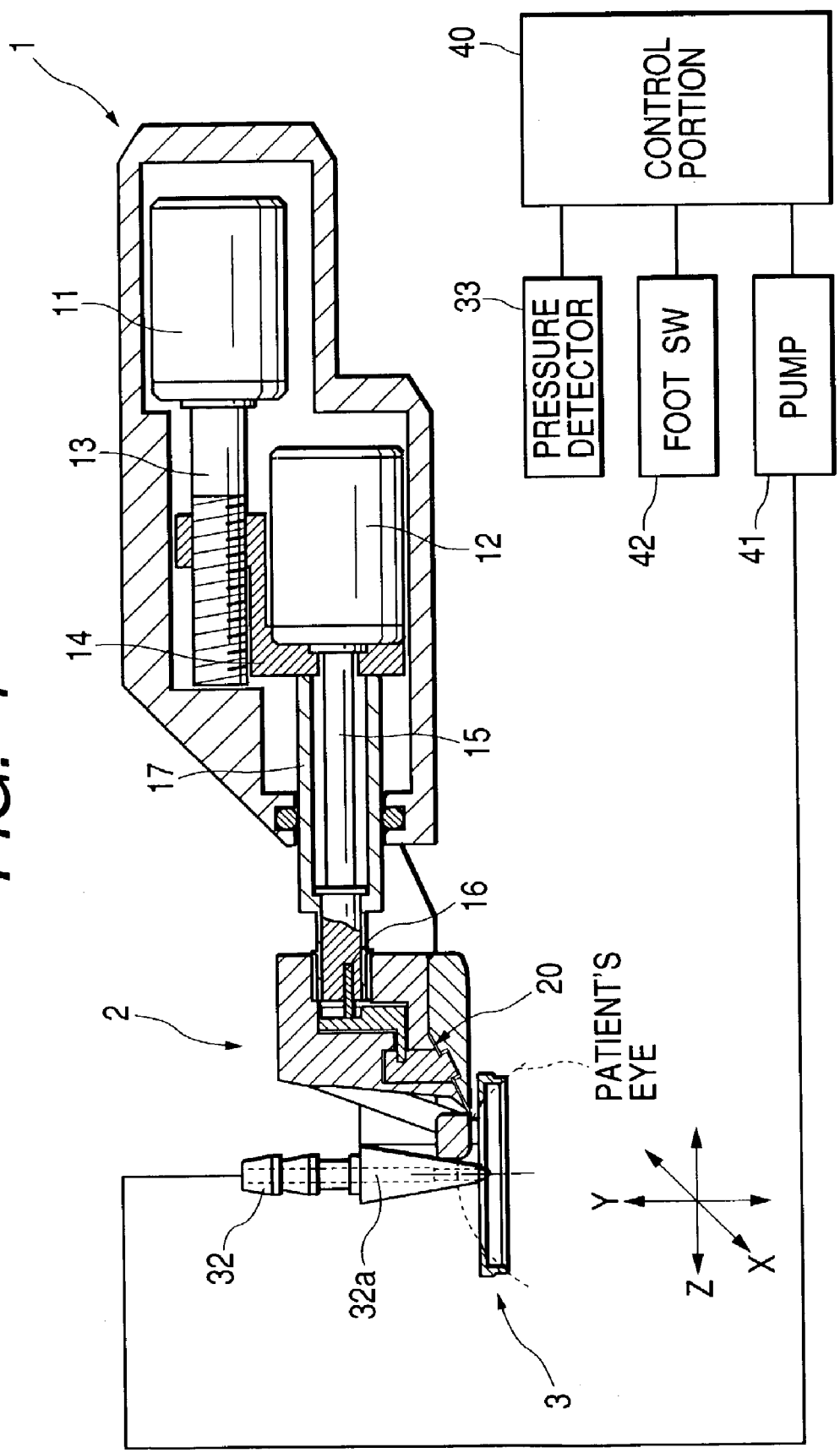
FIG. 1 is a sectional view and a block diagram showing the schematic structure of a corneal surgical apparatus according to a first embodiment of the invention.

Referring to the accompanying drawings, a description will be given of a first embodiment of the present invention. FIG. 1 is a cross-sectional view and a control system diagram of a corneal surgery apparatus in accordance with the first embodiment.

Reference numeral 1 denotes a main body. A suction unit 3 for fixing the apparatus to the patient's eye and a cutting unit 2, which has a blade 20 for incising and separating the corneal epithelium and is adapted to move (translate) rectilinearly on the suction unit 3, are provided on the front side (left-hand side in FIG. 1) of the main body 1.

A translating motor 11 for rectilinearly moving (translating) the cutting unit 2 (the blade 20) in a incising and separating direction corresponding to the forward and backward direction (in the direction) and an oscillating motor 12 for imparting oscillations in the lateral direction (in the X direction) to the blade 20 are installed in the main body 1. A feed screw 13 is coupled to a rotating shaft of the motor 11, which has a threaded portion corresponding in length to the rectilinear movement (translation) or travel of the cutting unit 2. An attaching member 14 is threadedly engaged with the screw 13. The motor 12 as well as a connecting member 17 to which the cutting unit 2 is connected are fixed to the attaching member 14. As the motor 11 is rotated forwardly or reversely, the motor 12 and the connecting member 17 move forwardly or backwardly (in the Z direction) through the screw 13 and the attaching member 14, thereby causing the cutting unit 2 to move (translate) forwardly or backwardly. Further, the connecting member 17 rotatably holds a rotating shaft 15. An eccentric pin 16 is embedded or protruded on a distal end of the rotating shaft 15 at a position offset from the center of rotation, and the eccentric pin 16 imparts lateral oscillations to the blade 20.

Figure 2:
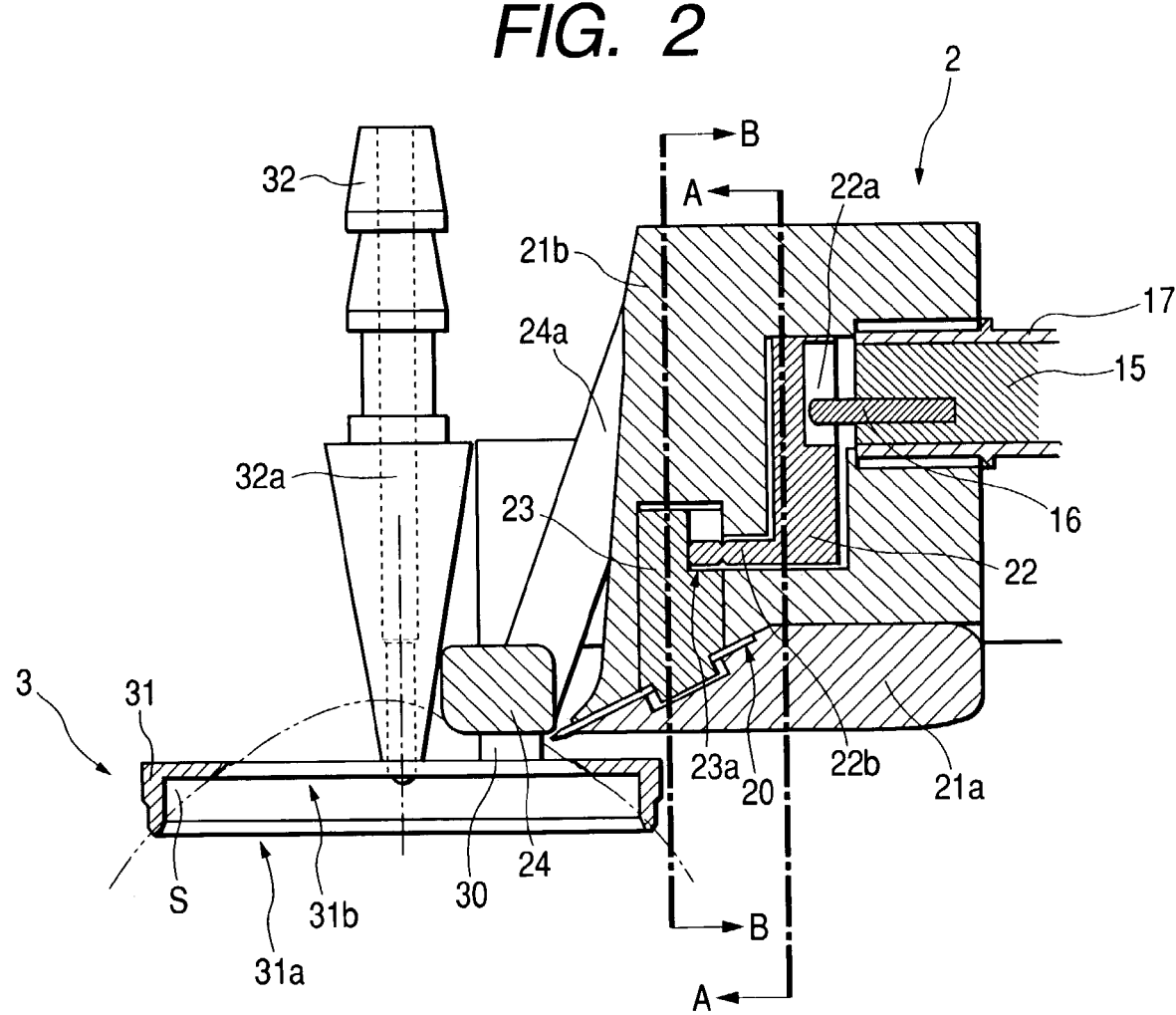
FIG. 2 is an enlarged view of FIG. 1, illustrating a cutting unit and a suction unit.
Figure 3:
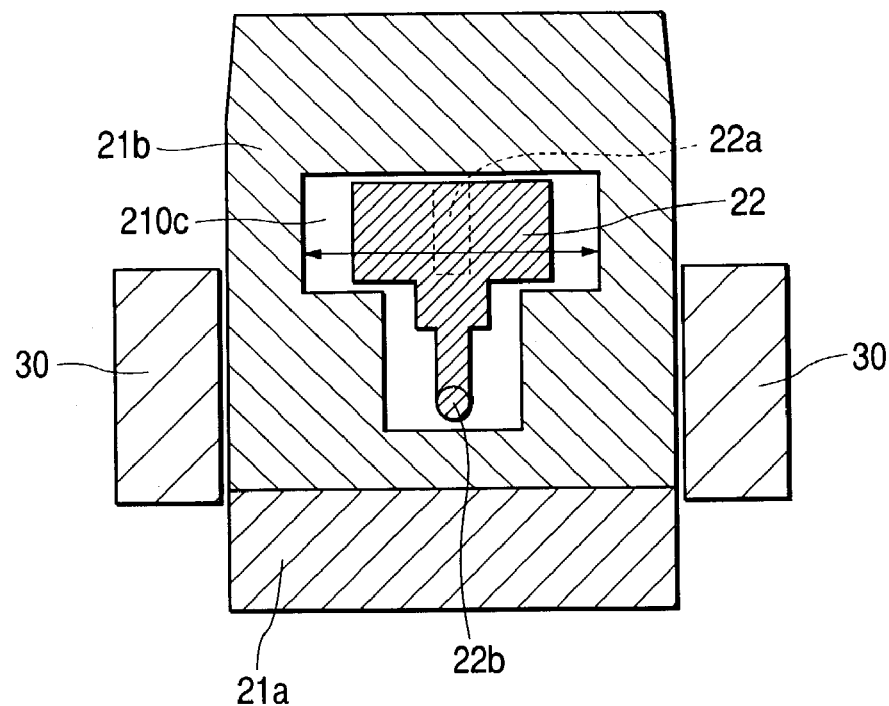
FIG. 3 is a sectional view taken along a line A—A in FIG. 2.
Figure 4:
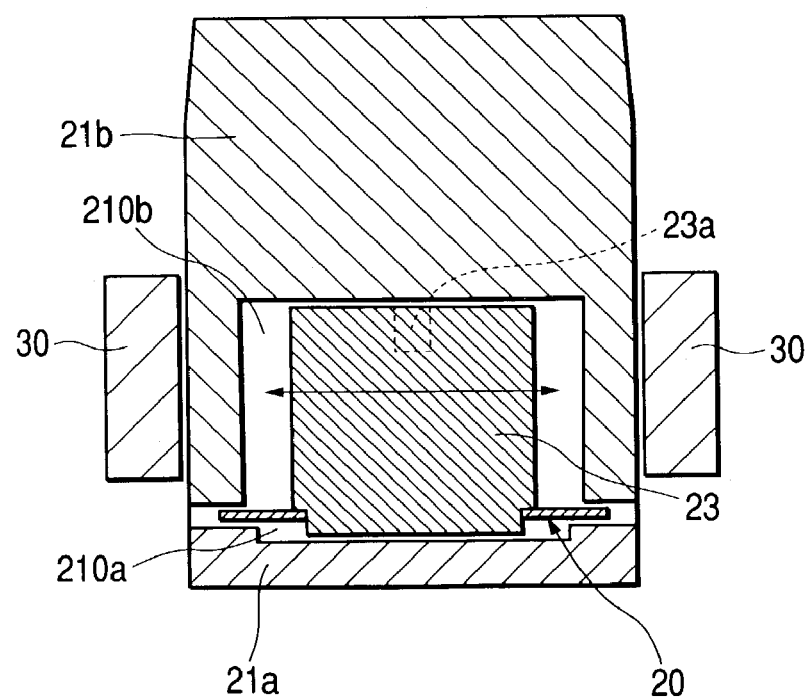
FIG. 4 is a sectional view taken along a line B—B in FIG. 2.

FIG. 2 is an enlarged view of the cutting unit 2 and the suction unit 3 shown in FIG. 1. FIG. 3 is a cross-sectional view taken along line A—A of FIG. 2. FIG. 4 is a cross-sectional view taken along line B—B of FIG. 2.

The cutting unit 2 is comprised of a blade holder 21a and a holder block 21b for holding the blade 20 in such a manner as to permit lateral oscillations; a first oscillation transmitting member 22 for transmitting the lateral oscillations generated by the eccentric pin 16; a second oscillation transmitting member 23 for transmitting the lateral oscillations by the first transmitting member 22 to the blade 20, and a cornea applanating member 24 fixed to the block 21b by means of an attaching member 24a. A rotation hole into which the rotating shaft 15 is inserted is provided inside the block 21b, and a tip portion of the connecting member 17 is fixed thereto.

A metal blade having a blade edge of stainless steel, steel, or the like or a mineral blade having a blade edge of diamond, sapphire or the like is used as the blade 20. The blade 20 is held between the holder 21a and the block 21b at about 25 degrees with respect to the horizontal plane in such a manner as to be capable of undergoing the lateral oscillations. A shape of the blade edge of the blade 20 will be described hereinafter.

On the holder 21a side, a shallow recess 210a is formed at a portion where the blade 20 is placed, and the lateral width of the recess 210a is set to be larger than the oscillating width for the lateral oscillations of the blade 20. The blade holder 21a is detachably fixed to the holder block 21b by a screw (not shown). The blade 20 can be removed with the second transmitting member 23 by detaching the blade holder 21.

The first transmitting member 22 is held within a receiving groove 210c formed in the block 21b in such a manner as to be capable of undergoing the lateral oscillations. The upper and lower portions of the first transmitting member 22 in the vertical direction (in the Y direction) is held by the block 21b. A vertical groove 22a for engagement with the eccentric pin 16 is formed in the first transmitting member 22. When the rotating shaft 15 is rotated by the rotative driving of the motor 12, the eccentric pin 16 engaged with the vertical groove 22a applies a lateral driving force to the first transmitting member 22. This causes the first transmitting member 22 to oscillate laterally.

The second transmitting member 23 is held within the receiving groove 210b formed in the block 21b in such a manner so as to be capable of undergoing the lateral oscillations. The upper portion and the lower portion of the second transmitting member 23 in the vertical direction are respectively held by the block 21b and the blade holder 21a. The first transmitting member 22 is provided at its lower portion with a protrusion 22b projected to the blade 20 side, and the second transmitting member 23 is formed with a vertical groove 23a engaged with the protrusion 22b. As the first transmitting member 22 is oscillated laterally by the rotation of the rotating shaft 15 (circumferential or circular motion of the eccentric pin 16), the protrusion 22b engaged with the vertical groove 23a is laterally oscillated, thereby applying lateral kinematics force to the second transmitting member 23. Accordingly, the second transmitting member 23 is laterally oscillated together with the blade 20 fixed to the second transmitting member 23.

The cornea applanating member 24 is provided on the front side (left-hand side in FIG. 2) of the blade 20 so as to flatly applanate the cornea of the patient's eye in advance of incising and separating the corneal epithelium by the blade 20. Since the blade 20 incises and separates the corneal epithelium thus applanated flatly by the applanating member 24, a flap in which the corneal epithelium is separated from the Bowan's membrane is formed.

Incidentally, in order to separate the corneal epithelium, the edge of the blade 20 is located below the lower surface of the applanating member 24 by a thickness of the corneal epithelium. The distance between the lower surface of the applanating member 24 and the edge of the blade 20 is preferably set to be about 100 to 300 µm, and is set to be about 200 µm in this embodiment.

The suction unit 3 includes a fixing member 30, a suction ring 31, a suction pipe 32 and the like. The suction ring 31 is fixed to the main body by the fixing unit member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye in place for surgery, the cornea of the patient's eye projects upward from the opening 31b, and a lower end portion of the suction ring 31 and an opening end portion (a periphery) of the opening 31b are caused to abut against the patient's eye to define a space S for suction.

The suction pipe 32 is embedded on (i.e. projectingly provided on) the suction ring 31, and connected through an unillustrated vacuum tube to a pump 41. The vacuum tube is elongated to the pump 41. A suction passage 32a provided inside the suction pipe 32 communicates with the recessed portion 31a, and as the air inside the space S is sucked and discharged by the pump 41 through the passage 32a, the suction ring 31 is vacuum-fixed to the patient's eye.

In addition, an unillustrated pressure detection pipe is embedded on the suction ring 31, and the pressure detection pipe is connected to a pressure detector 33 through an unillustrated tube. The detector 33 detects, through the pressure detection pipe, the air pressure inside the space S sucked by the pump 41. A control portion 40 controls the operation of the motor 11, the motor 12, the pump 41, etc. on the basis of the air pressure detected by the detector 33.

Figure 5A:
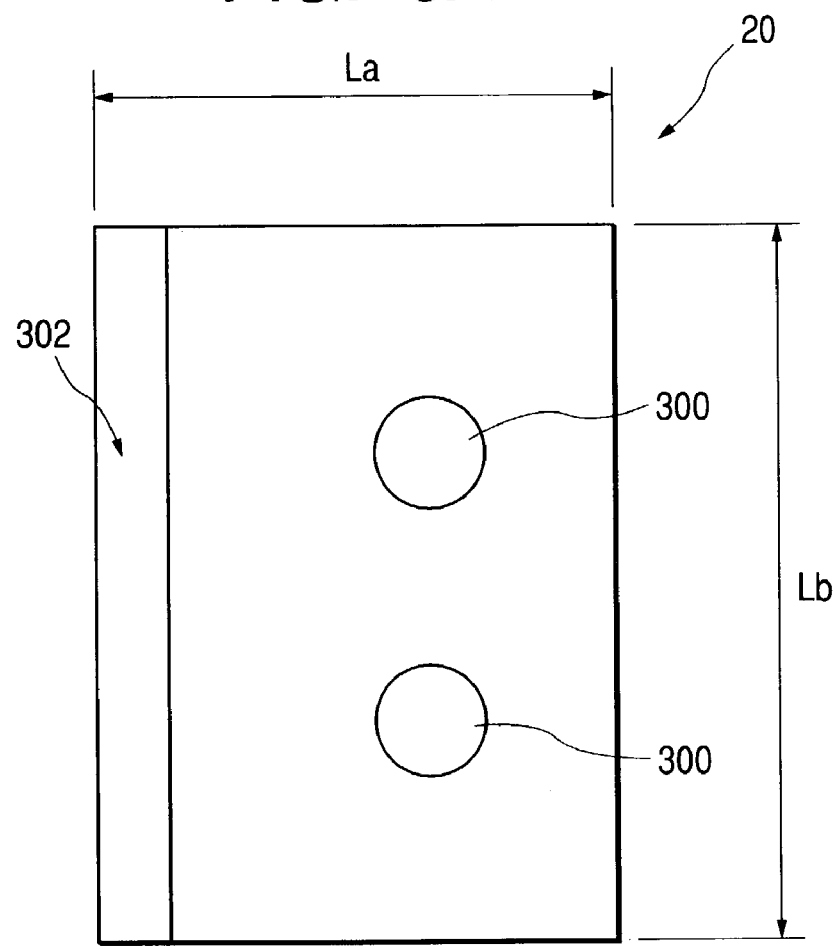
FIG. 5A is a plan view showing a blade according to the first embodiment.
Figure 5B:
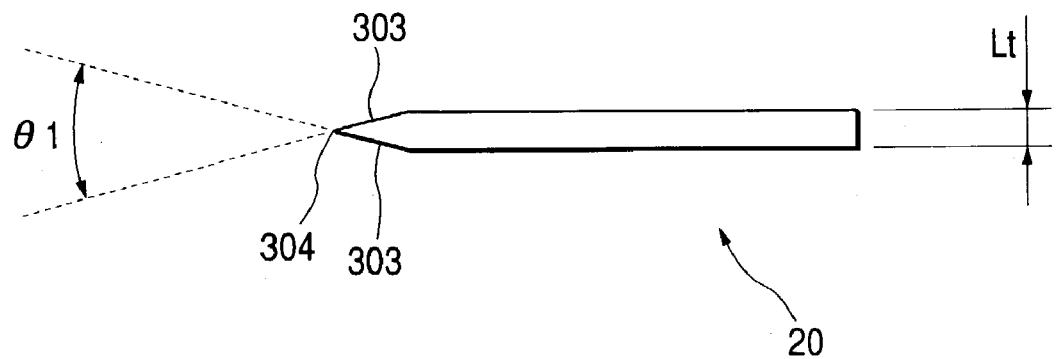
FIG. 5B is a sectional view showing the blade according to the first embodiment.

Next, the shape of the blade 20 will be described. FIG. 5A is a plan view showing the blade 20 and FIG. 5B is a sectional view showing the blade 20. The blade 20 has a width La of approximately 8 mm, a length Lb of approximately 12.9 mm and a thickness Lt of approximately 0.25 mm. The reference numeral 300 denotes two holes to which the second transmitting member 23 is fitted. A blade portion 302 having two upper and lower blade surfaces 303 is formed on the front side of the blade 20. Both of the blade surfaces 303 are formed with an inclination at the same angle with respect to a center line of the thickness Lt. An angle θ1 formed by both of the blade surfaces 303 is set to be approximately 10 to 70 degrees, preferably approximately 10 to 50 degrees, and more preferably approximately 15 to 40 degrees, and is set to be approximately 19 degrees in the embodiment. Moreover, both of the blade surfaces 303 are polished to maintain a sharpness. In the case in which an edge portion 304 on the tip side is to be further sharpened, the angle θ1 formed by both of the blade surfaces 303 is increased stepwise toward the edge portion 304.

Figure 6A:
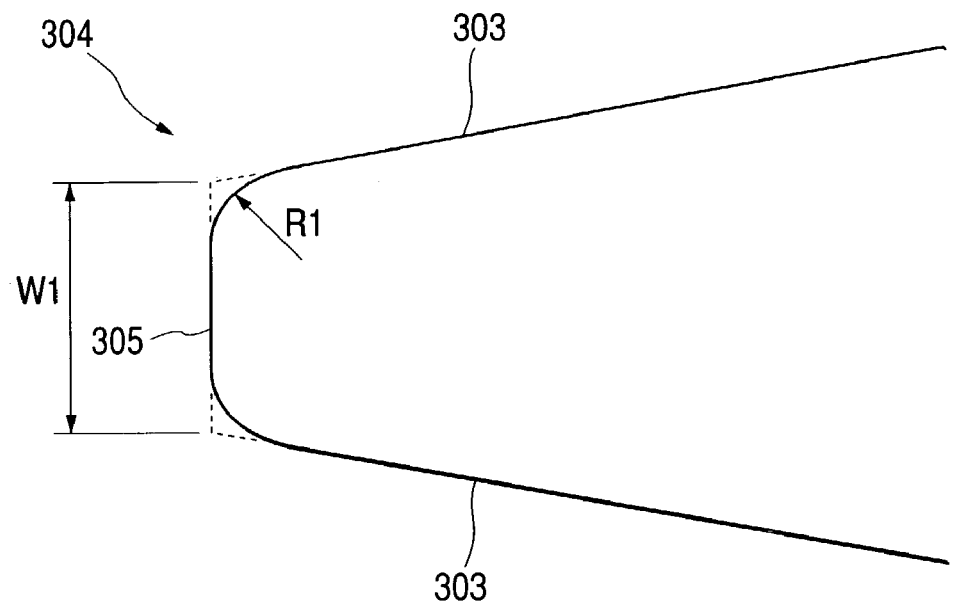
FIG. 6A is an enlarged view of FIG. 5B, illustrating the edge of the blade.
Figure 6B:
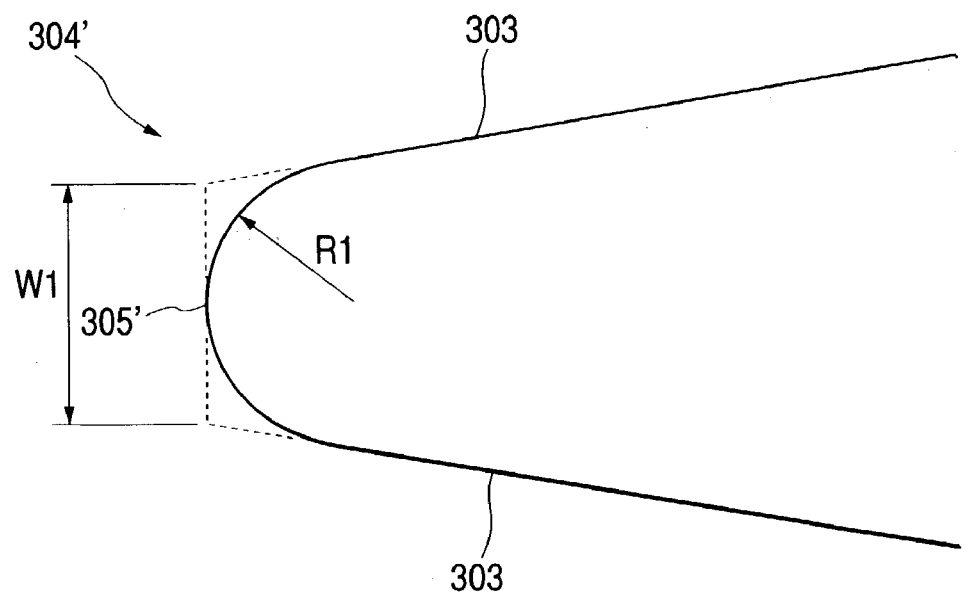
FIG. 6B is an enlarged sectional view showing a variant of the edge of the blade in FIG. 6A, FIGS. 7A and 7B are views showing an electron micrograph for the edge of a first blade used in an experiment.

FIG. 6A is an enlarged view of FIG. 5B, illustrating the edge portion 304. The edge portion 304 can incise a corneal epithelium and cannot incise a Bowman's membrane which is harder than the corneal epithelium. For this reason, a height W1 of an edge surface 305 of the edge portion 304 is set to be approximately 1 to 70 μm, preferably approximately 1 to 50 μm, and more preferably approximately 2 to 20 μm. The height W1 of the edge surface 305 is represented as a width of an intersection of the virtual extended surfaces of the blade surfaces 303 forming the angle θ1. The edge portion 304 is formed such that the edge surface 305 has a large plane. If the connecting portion of the edge surface 305 and the blade surface 303 is square, the Bowman's membrane can easily be incised. Therefore, the connecting portion has a curved surface (roundness). A radius of curvature RI is approximately 0.5 to 35 μm, and preferably approximately 0.5 to 25 μm. FIG. 6B shows a variant of the edge portion 304 in FIG. 6A. An edge portion 304' is formed such that an almost whole edge surface 305' has a curved surface (the almost whole edge surface 305' becomes a connecting portion with the blade surface 303 having a curved surface).

Description will be given to an operation for incising and separating a corneal epithelium using the apparatus described above. After the suction ring 31 is provided on a patient's eye and the pump 41 is then operated to suck air in the space S between the suction ring 31 and the patient's eye, thereby reducing the air pressure. Consequently, the suction ring 31 is adsorbed and fixed to the patient's eye. In response to the signal of a foot switch 42, the control portion 40 drives the motor 12 and the motor 11. Consequently, the cutting unit 2 is moved (translated) rectilinearly in the direction of incision and separation with the laterally oscillated blade 20 held.

A corneal epithelium is incised by the edge portion 304 of the blade 20 moved (translated) rectilinearly with the lateral oscillations. Then, the edge portion 304 reaches the Bowman's membrane under the corneal epithelium, and the harder Bowman's membrane than the corneal epithelium is not incised because of the shape of the edge portion 304 described above and the blade 20 is moved (translated) rectilinearly to slide over the Bowman's membrane. Consequently, the corneal epithelium is separated from the Bowman's membrane (or a basement membrane under the corneal epithelium) and a flap is formed. At this time, the translating speed of the blade 20 is set to be approximately 0.4 to 6 mm/sec and the lateral oscillation frequency is set to be approximately 5,000 to 25,000 rpm. When the height W1 of the edge surface 305 of the blade 20 is approximately 2 to 10 μm, the translating speed of the blade 20 is preferably set to be approximately 2 mm/sec and the lateral oscillation frequency is set to be approximately 9,000 rpm. The lateral oscillation of the blade 20 has a width of approximately 2 mm.

Figure 7A:
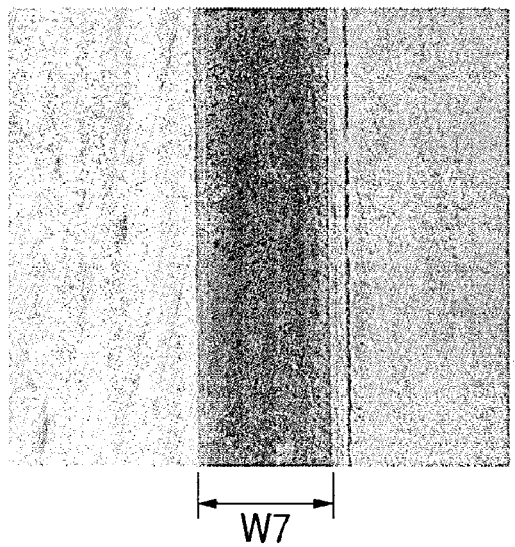
Figure 7B:
Figure 8A:
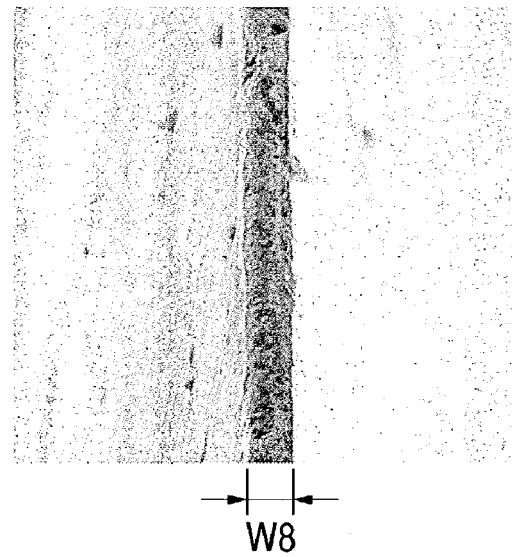
FIGS. 8A and 8B are views showing an electron micrograph for the edge of a second blade used in an experiment.
Figure 8B:
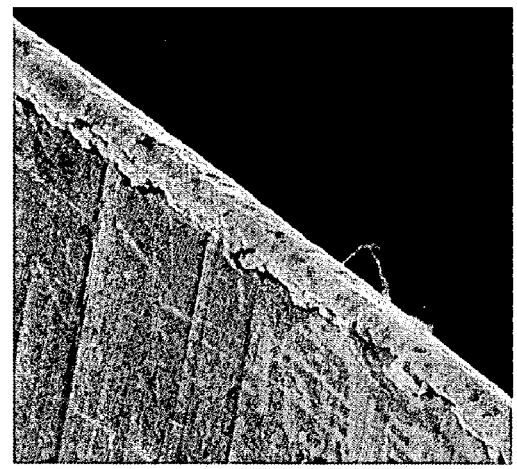
Figure 9A:
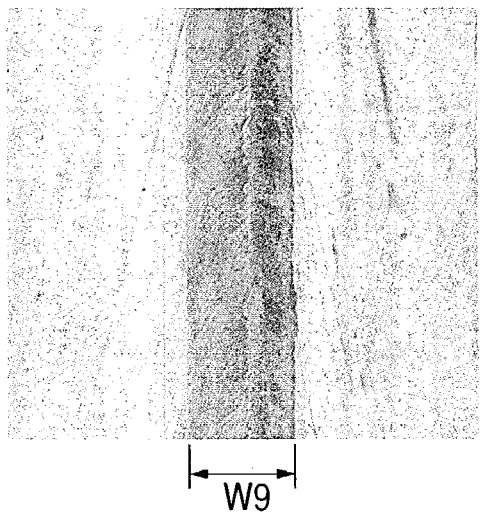
FIGS. 9A and 9B are views showing an electron micrograph for the edge of a third blade used in an experiment.
Figure 9B:
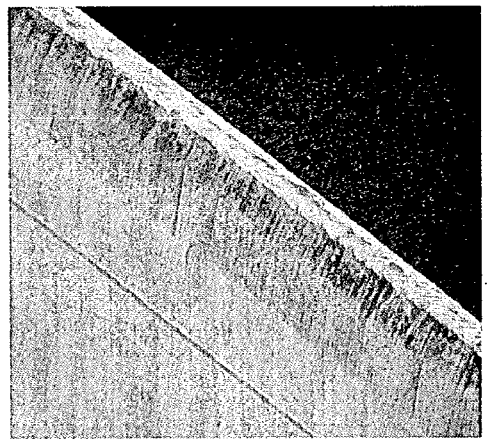

Referring to the incision and separation of the corneal epithelium by the blade 20 described above, an experiment was carried out by using a pig eye. FIGS. 7 to 9 show the electron micrographs (a magnification of 3,000) of the edges of three kinds of blades used in the experiment, and FIGS. 7A, 8A and 9A are views showing the edge seen from a front and FIGS. 7B, 8B and 9B are views showing the edge seen obliquely and laterally. The translating speed of the blade 20 in all the experiments is approximately 2 mm/sec and the lateral oscillation frequency is approximately 9000 rpm. Moreover, the corneal epithelium of the pig eye has a thickness of approximately 100 μm.

The edge of a first blade shown in FIGS. 7A and 7B is formed such that the edge surface has a large plane as shown in FIG. 6A. The edge surface has a height W7 of approximately 6 μm, and the connecting portion of the edge surface and the blade surface has a curved surface (a radius of curvature is approximately 1 μm). A flap in which only the corneal epithelium is separated could be formed smoothly by the first blade.

The edge surface of a second blade shown in FIGS. 8A and 8B has a height W8 of approximately 2 μm and is formed such that the almost whole edge surface has a curved surface as shown in FIG. 6B. A part of the curved surface has a portion (burr) which is not smooth. By the second blade, therefore, the separation of the corneal epithelium could be smoothly carried out by approximately 80% and approximately 20% of the residual corneal epithelium was incised up to a corneal stroma. More specifically, the corneal epithelium can be separated smoothly in a portion in which the curved surface is smooth.

The edge surface of a third blade shown in FIGS. 9A and 9B has a height W9 of approximately 5 μm, and the connecting portion of the edge surface and the blade surface does not have a curved surface but is square. By the third blade, therefore, the separation of the corneal epithelium can be smoothly carried out by approximately 50% and approximately 50% of the residual corneal epithelium was incised up to a corneal stroma.

From the results of the experiments, if the connecting portion of the edge surface and the blade surface has the curved surface with the edge surface having a height of approximately 2 µm, only the corneal epithelium can be separated without incising the corneal stroma. In consideration of the fact that the pig eye does not have the Bowman's membrane but a human eye has a much harder Bowman's membrane than the corneal stroma, it is possible to separate only the corneal epithelium without incising the Bowman's membrane even if the height of the edge surface is set to be approximately 1 µm.

Figure 10A:
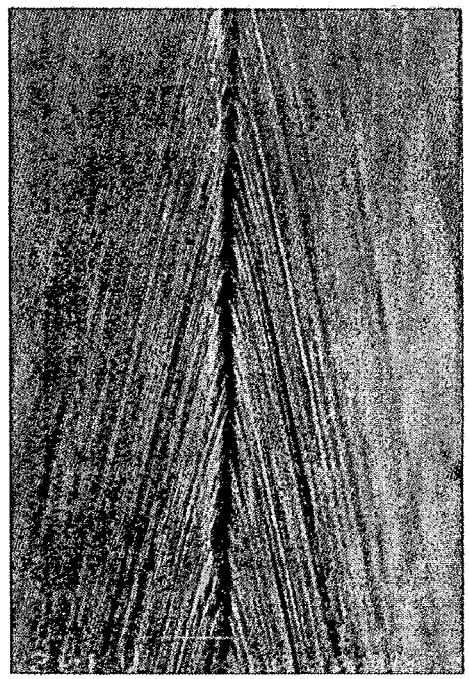
FIGS. 10A and 10B are views showing an electron micrograph for the edge of a blade for LASIK.
Figure 10B:
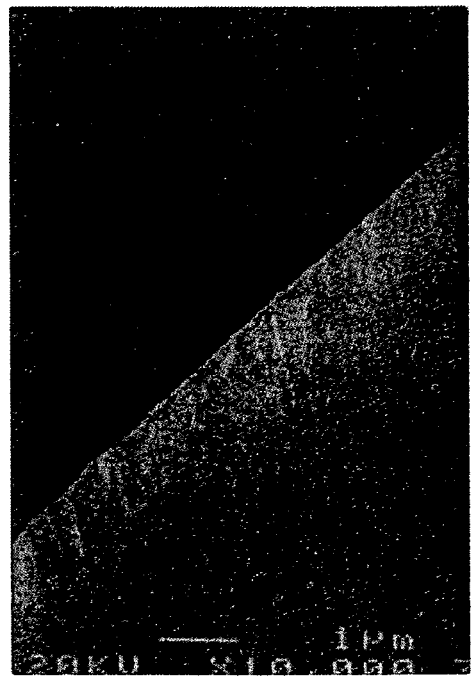

FIGS. 10A and 10B show the electron micrographs (a magnification of 10,000) of the edge of a blade for conventional LASIK. FIG. 10A is a view showing the edge seen from a front and FIG. 10B is a view showing the edge seen obliquely and laterally. It is apparent that the height of the edge surface is much shorter than 1 µm (more sharpened) in order to incise a hard Bowman's membrane in the blade for LASIK.

Figure 11:
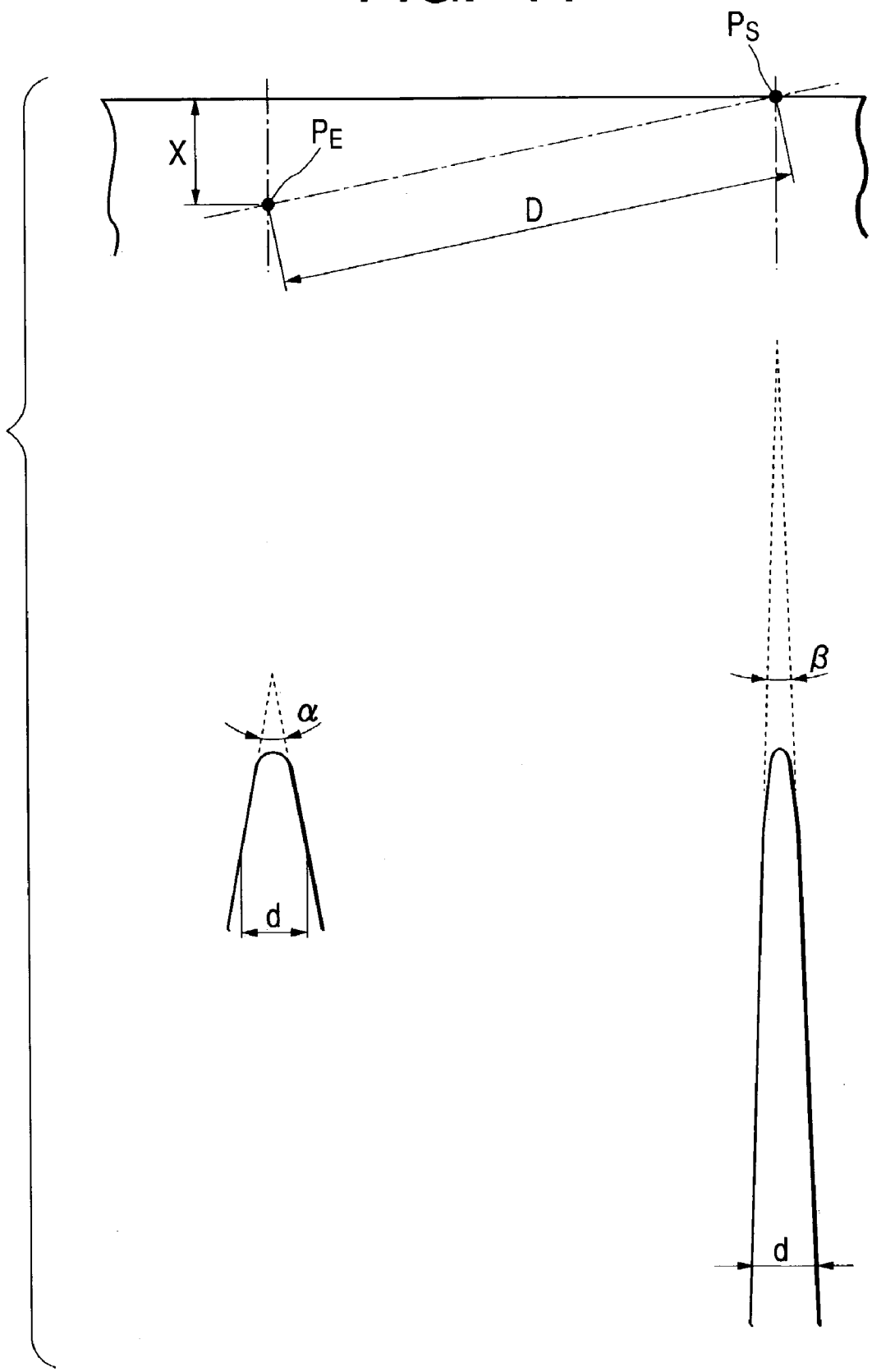
FIG. 11 is a view illustrating the relationship between the rectilinear movement and lateral oscillation of the blade and the incising angle of an edge.

Next, description will be given to the relationship between the rectilinear movement and lateral oscillation (lateral sliding) of the blade 20 and the incising angle of the edge (the height of the edge surface) with reference to FIG. 11. It is assumed that the blade 20 is moved rectilinearly by an x distance in an upward direction while the blade 20 is slid in a right lateral direction in FIG. 11. At this time, an abutment point PS of the edge is relatively moved in a track of PS-PE over the blade and a movement distance is represented by D. If the thickness from the edge to a point x is represented by d, an incising angle β at this time forms the same shape as the sectional shape of the edge passing through PS-PE and a more sharpened tip than an actual edge angle α (a section in the direction of an x distance). Accordingly, in the case in which the height of the edge surface of the blade 20 is set to be greater than approximately 6 µm in the experiment (for example, in the case of approximately 50 µm), a lateral oscillation speed (frequency) is relatively increased with respect to a translating speed so that the edge can be apparently sharpened to incise the corneal epithelium.

On the other hand, in the case in which the height of the edge surface of the blade 20 is set to be smaller than approximately 2 µm, it is preferable that the lateral oscillation speed (frequency) should be relatively reduced with respect to the translating speed. Consequently, it is possible to prevent the incision of the Bowman's membrane and the corneal stroma.

By setting the height of the edge surface of the blade 20 and the translating speed and lateral oscillation speed (frequency) of the blade corresponding thereto, a corneal epithelium flap can easily be formed. The flap edge also becomes smoother than that of a conventional golf knife. Moreover, the blade 20 can be exchanged. Therefore, it is also possible to form a flap incised like a layer up to the corneal stroma by an exchange into the blade for LASIK.

While the blade 20 is translated rectilinearly in the embodiment, it may be translated annularly. Moreover, only the lateral oscillations of the blade may be carried out by a driving source such as a motor and the rectilinear movement (translation) flap be carried out manually.

Second Embodiment

Figure 12:
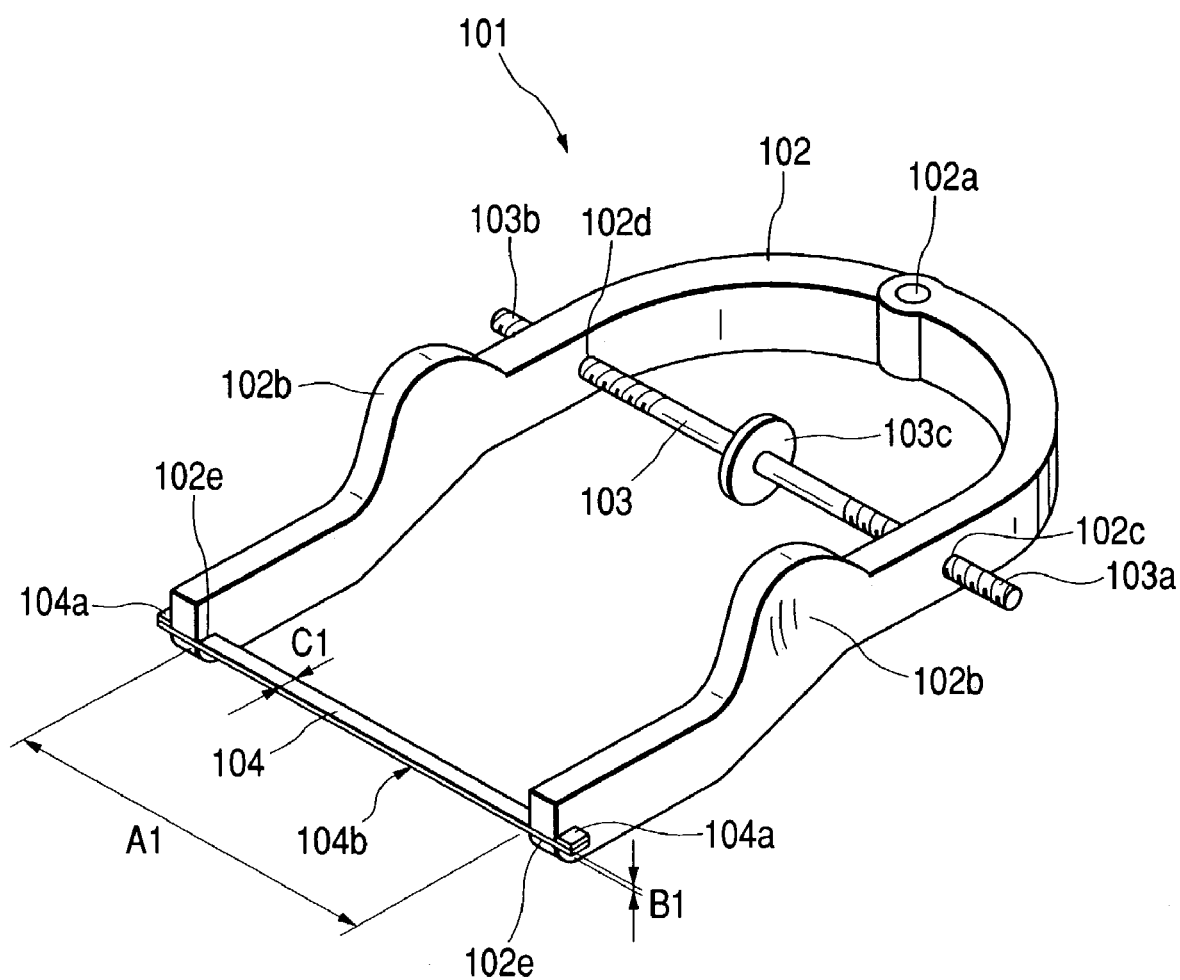
FIG. 12 is an outside view showing the schematic structure of a corneal surgical apparatus according to a second embodiment of the invention.

Next, a second embodiment of the invention will be described with reference to the drawings. FIG. 12 is an outline view showing the schematic structure of a corneal, surgical apparatus according to the second embodiment.

The reference numeral 101 denotes an apparatus body having a blade 104 for separating a corneal epithelium and an arc-shaped flame 102 to be a holder for holding the blade 104. The frame 102 is pivotable around a shaft 102*a* and can regulate a spacing (a tensile strength) between opposite ends of the frame 102 for holding the blade 104. The reference numeral 102*b* denotes a holding portion which is held by an operator with fingers during surgery and is provided integrally with the frame 102.

The reference numeral 103 denotes a screw bar to open and close the frame 102 like a pair of compasses to be used for drafting. The reference numeral 102*c* denotes a female screw provided on the frame 102 and engaged with a male screw 103*a* of the screw bar 103, and the female screw 102*c* and the male screw 103*a* are right-handed screws. Moreover, the reference numeral 102*d* denotes a female screw provided on the frame 102 and engaged with a male screw 103*b* of the screw bar 103, and the female screw 102*d* and the male screw 103*b* are left-handed screws. The reference numeral 103*c* denotes a knob provided in the central part of the screw bar 103. The opposite ends of the frame 102 can be opened and closed by rotating the knob 103*c* while the shaft 102*a* is set at a rotation center.

The blade 104 is formed of a band-shaped thin steel plate and is fitted in an attachment groove 102*e* formed on the opposite ends of the frame 102, respectively. Bent portions 104*a* are provided on the opposite ends in the longitudinal direction of the blade 104 and are caught on the outside of the attachment groove 102*e*. In the case in which the thickness of the blade 104 is small, a thick block may he fixed in place of the bent portion 104*a*. Metal such as stainless or steel is utilized for the material of the blade 104 (thin steel plate).

A length A1 (a spacing between opposite ends of the frame 102) of an edge portion 104*b* of the blade 104 estimates the amount of movement of the lateral oscillations of the blade 104, and is preferably approximately 10 mm to 30 mm and is approximately 15 mm in the embodiment. It is preferable that a thickness B1 of the blade 104 should be more or less thin in order to smoothly separate the corneal epithelium. If the thickness is too decreased, a strength is reduced. Therefore, the thickness B1 is preferably approximately 5 to 70 µm and is approximately 20 µm in the embodiment. It is preferable that a width C1 of the blade 104 should be more or less great in order to maintain the tensile strength of the blade 104. If the width C1 is too increased, the separated corneal epithelium is apt to stick. Therefore, the width C1 is preferably approximately 0.3 to 5 mm, more preferably approximately 0.5 to 2 mm and approximately 1 mm in the embodiment. In the case in which the thickness B1 is reduced, it is preferable that the width C1 should be increased relatively.

Figure 13A:
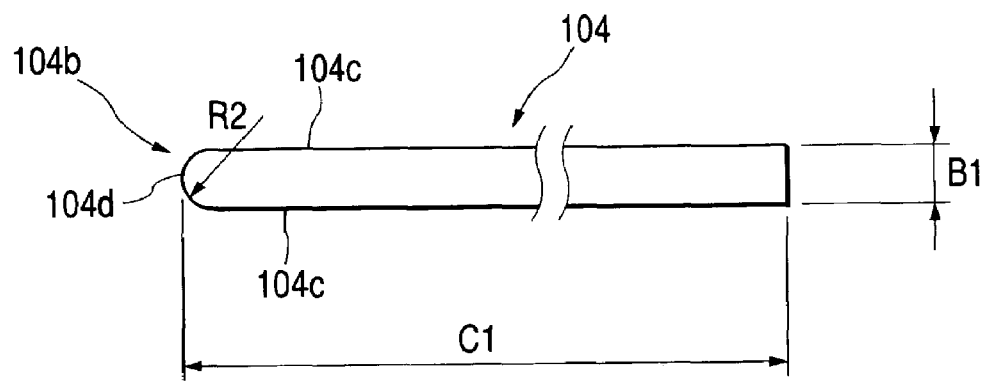
FIG. 13A is a sectional view showing a blade according to the second embodiment.

FIG. 13A is a sectional view showing the blade 104. A blade surface 104*c* is formed on the upper and lower surfaces of the edge portion 104*b* of the blade 104 (the two blade surfaces 104*c* are provided in parallel with each other), and the connecting portion of an edge surface 104*d* and the blade surface 104*c* is caused to have a curved surface (roundness). It is preferable that a radius of curvature R2 should be approximately 0.5 µm or more.

Figure 13B:
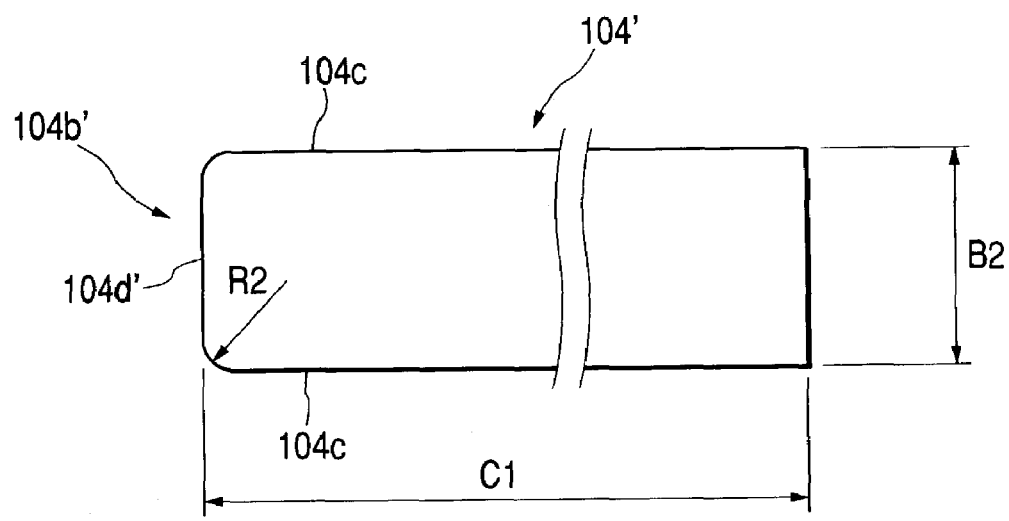
FIG. 13B is a sectional view showing a variant of the blade in FIG. 13A.
Figure 13C:
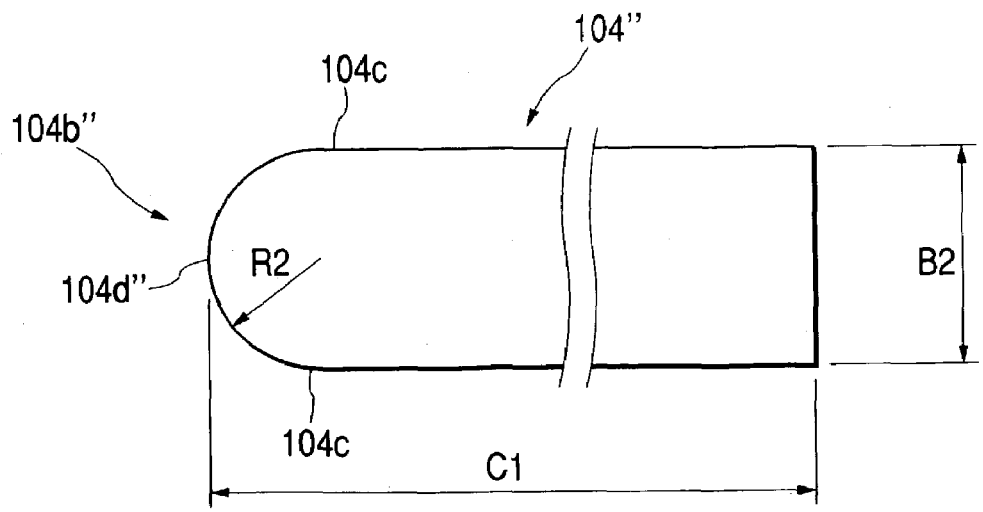
FIG. 13C is a sectional view showing a variant of the blade in FIG. 13A.

FIGS. 13B and 13C show a variant of the blade 104 in FIG. 13A. Blades 104' and 104" have a thickness B2 of approximately 70 µm. An edge portion 104*b'* of the blade 104' is formed such that an edge surface 104*d'* has a large plane. An edge portion 104*b"* of the blade 104" is formed such that an almost whole edge surface 104*d"* has a curved surface. A radius of curvature R2 of the curved surface can be varied with respect to the thickness B2 (B1). For example, the radius of curvature R2 is approximately 35 µm in the case of the edge portion 104*b"*.

In the case in which the blade 104 is to be attached to the frame 102, first of all, the knob 103c is turned to reduce the spacing between opposite ends of the frame 102 and the blade 104 is fitted in the attachment groove 102e. Then, the knob 103c is turned in a reverse direction to increase the spacing between both ends of the frame 102. Thereafter, the knob 103c is turned until the bent portion 104a is pushed against the attachment groove 102e. Thus, the blade 104 is fixed to the attachment groove 102e. Furthermore, the knob 103c is turned to regulate the tension of the blade 104 such that the cornea is rectilinearly flattened when the lower surface of the blade 104 (or the edge surface 104d) is pushed against the cornea.

Figure 14:
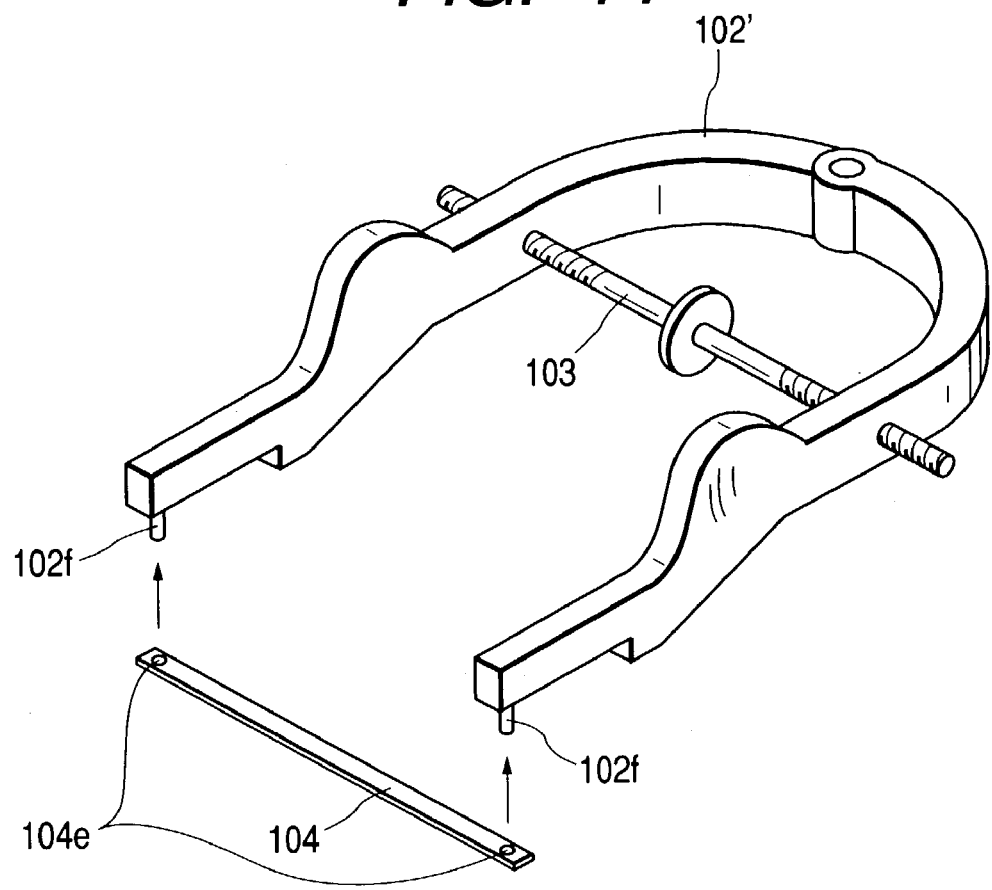
FIG. 14 is an outside view showing a variant of the corneal surgical apparatus in FIG. 12.

As a method of fixing the blade, holes 104'e maybe formed through the blade 104', through which shafts 102f provided on opposite ends of a frame 102' pass to fix the blade 104' as shown in FIG. 14 illustrating the variant of the apparatus in FIG. 12.

Figure 15:
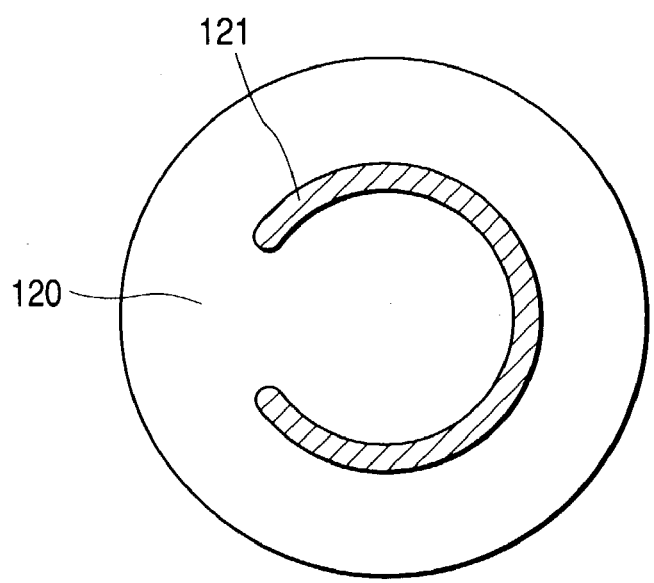
FIG. 15 is a view showing an annular cut formed on a corneal epithelium.
Figure 16:
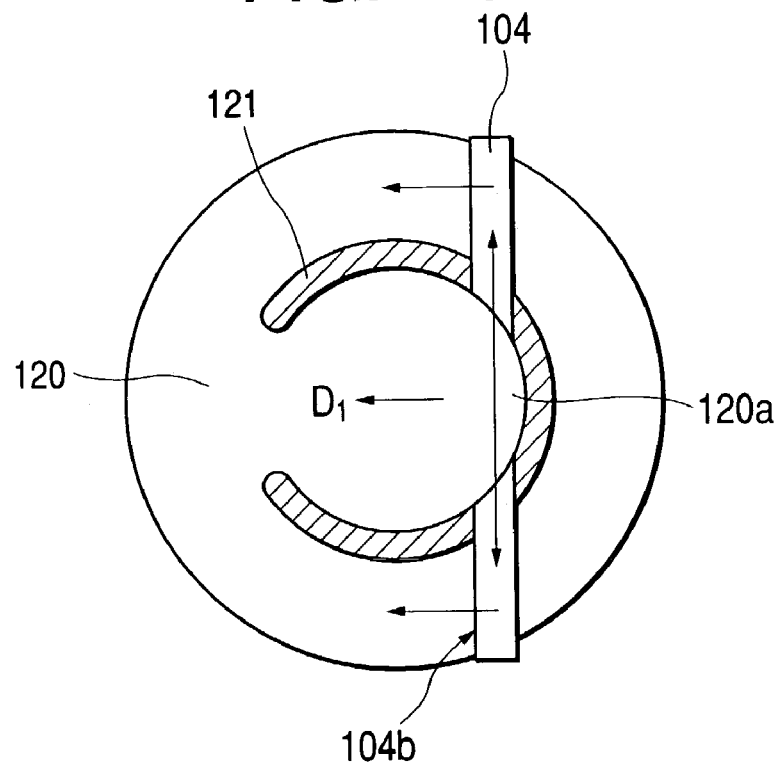
FIG. 16 is a view showing a method of forming a corneal epithelium flap.
Figure 17:
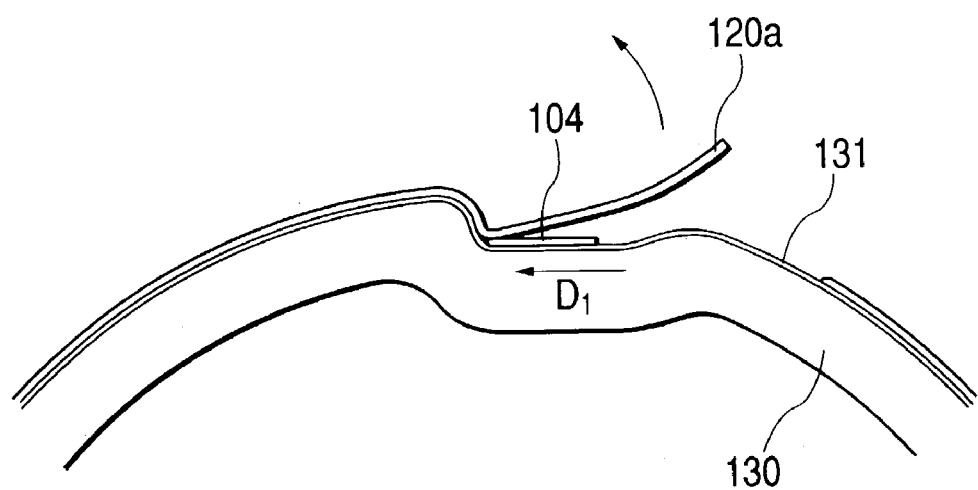
FIG. 17 is a view showing the method of forming a corneal epithelium flap.

Description will be given to an operation for incising and separating a corneal epithelium using the apparatus described above. As shown in FIG. 15, first of all, an annular (horseshoe-shaped) cut region 121 leaving a hinge in a corneal epithelium 120 is formed by using an epi-trephine or a golf knife to previously form an edge for preparing a flap. Next, the holding portion 102b of the frame 102 is held with fingers, and the blade 104 is inserted into the cut region 121 from the edge portion 104b and is laterally oscillated in a longitudinal direction, and simultaneously, is rectilinearly moved (translated) forward (in a D1 direction) so as to separate the corneal epithelium 120 as shown in FIG. 16. At this time, as shown in FIG. 17, the cornea is flattened at the lower surface of the blade 104. Although the edge portion 104b reaches a Bowman's membrane 131, the blade 104 is moved (translated) rectilinearly to slide over the Bowman's membrane 131 because of the shape of the edge portion 104b described above. Consequently, the corneal epithelium 120 is separated from the Bowman's membrane 131 (or a basement membrane under the epithelium) and a flap 120a is formed.

Figure 18A:
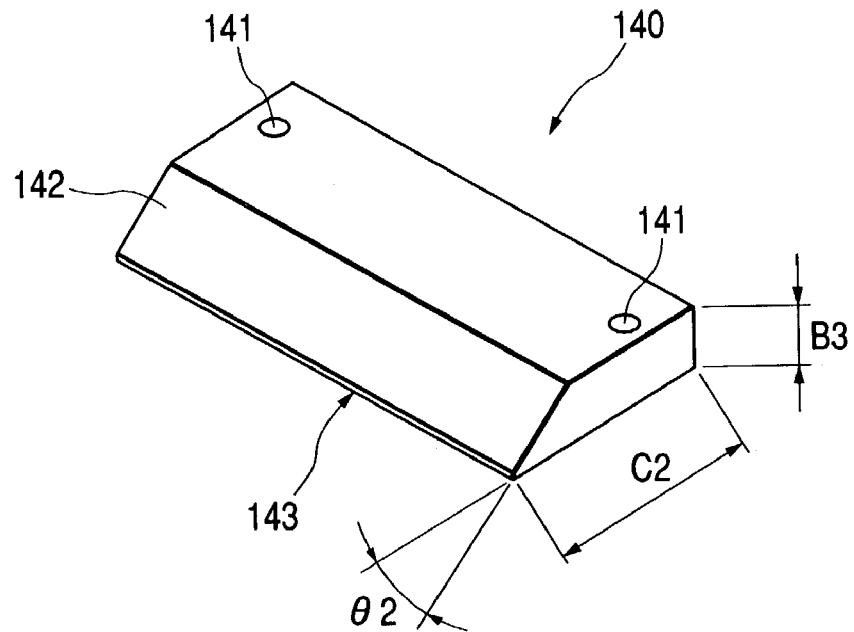
FIG. 18A is an outside view showing a variant of a blade in FIG. 14.

FIG. 18A is an outline view showing a variant of the blade 104' in FIG. 14. A blade 140 is wholly thickened to increase a strength and is prevented from being deformed when it is pushed against the cornea. A resin as well as metal such as stainless or steel are utilized for the material of the blade 140. A polyacetal resin may be used for the resin but a fluororesin (PTFE) having an excellent sliding property and a hydrophilic resin are preferred. In the case in which the blade 140 is formed of the resin, it has a lower rigidity than that of the metal and is thereby wedge-shaped. Moreover, if resin molding is carried out in consideration of a disposable type, a cost can be reduced.

In the blade 140, a thickness B3 is preferably approximately 0.2 to 3 mm and is approximately 2 mm in the embodiment. An edge portion 143 has a length which is preferably approximately 10 mm to 30 mm and is approximately 15 mm in the embodiment. Moreover, the blade 140 has a width C2 which is preferably approximately 1 to 5 mm in the case in which it is formed of metal, and is approximately 1 to 10 mm in the case in which it is formed of a resin having an excellent sliding property. In the embodiment, the resin having an excellent sliding property is used and the width C2 is set to be approximately 5 mm. Two holes 141 are for fixing the fix blade 140 to the shaft 102f provided on the opposite ends of the frame 102' by passing the shaft 102f therethrough.

Figure 18B:
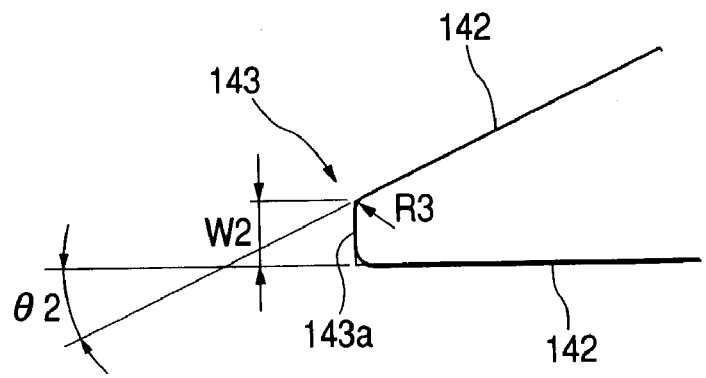
FIG. 18B is an enlarged sectional view showing the edge of the blade in FIG. 18A.
Figure 18C:
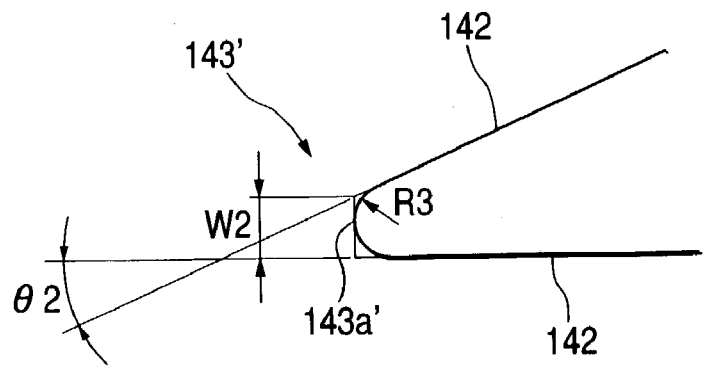
FIG. 18C is an enlarged sectional view showing a variant of the edge of the blade in FIG. 18B.

FIG. 18B is an enlarged sectional view of FIG. 18A, illustrating the edge portion 143. Two blade surfaces 142 are inclined and an angle θ2 formed by both blade surfaces 142 is preferably approximately 10 to 70 degrees and is approximately 25 degrees in the embodiment. An edge surface 143a has a height W2 which is preferably approximately 1 to 70 μm. The edge portion 143 is formed such that the edge surface 143a has a large plane, and the connecting portion of the edge surface 143a and the blade surface 142 has a curved surface in the same manner as in the previous example. A radius of curvature R3 is preferably approximately 0.5 to 35 μm. FIG. 18C shows a variant of the edge portion 143 in FIG. 18B, and an edge portion 143' is formed such that an almost whole edge surface 143a' has a curved surface.

While the lateral oscillations of the blade is carried out manually in the embodiment, it may be performed by a power source such as a motor as in the first embodiment.

What is claimed is:

1. A blade for corneal surgery for separating a corneal epithelium in a flap shape from a Bowman's membrane, the blade being used by being attached to a corneal surgical apparatus, the blade comprising:
   an upper blade surface to be positioned at the corneal epithelium side at the time of separation of the corneal epithelium;
   a lower blade surface to be positioned at the Bowman's membrane side at the time of the separation of the corneal epithelium; and
   an edge surface connecting the upper and lower blade surfaces, wherein
   the edge surface has a height of 1 to 70 μm and a connecting portion with each of the upper and lower blade surfaces, the connecting portion having a curved surface with a radius of curvature of 0.5 to 35 μm, so that the blade can incise the corneal epithelium and cannot incise the Bowman's membrane.

2. The blade according to claim 1, wherein an angle formed by the upper and lower blade surfaces is 10 to 70 degrees.

3. The blade according to claim 2, wherein
   the height of the edge surface is 1 to 50 μm,
   the angle formed by the upper and lower blade surfaces is 10 to 50 degrees, and
   the radius of curvature of the curved surface in the connecting portion is 0.5 to 25 μm.

4. A corneal surgical apparatus having the blade according to claim 1 further comprising a holder for detachably holding the blade.

5. The corneal surgical apparatus according to claim 4, further comprising:
   an oscillating unit which laterally oscillates the blade, and
   a translating unit which moves and translates the blade in a direction of the separation.

6. The corneal surgical apparatus according to claim 5, wherein a lateral oscillation frequency is 5,000 to 25,000 rpm and a translating speed is 0.4 to 6 mm/sec.

7. The blade according to claim 1, wherein each of the upper and lower blade surfaces is formed with an inclination toward a centerline of the edge surface.

8. The blade according to claim 1, wherein the blade is attached to a corneal surgical apparatus so that a centerline of the edge surface is inclined with respect to a horizontal plane.

* * * * *